United States Patent

Neward

[11] Patent Number: 5,803,926
[45] Date of Patent: Sep. 8, 1998

[54] DOUBLE HANDLED VACUUM EXTRACTOR

[75] Inventor: Theodore C. Neward, Claremont, Calif.

[73] Assignee: Pristech, Inc., San Antonio, Tex.

[21] Appl. No.: 488,492

[22] Filed: Jun. 7, 1995

[51] Int. Cl.[6] ............................ A61B 17/42; A61B 17/46
[52] U.S. Cl. ......................... 606/122; 606/123; 606/124
[58] Field of Search ................................... 606/122, 123, 606/124; 604/74

[56] References Cited

U.S. PATENT DOCUMENTS

| | | | |
|---|---|---|---|
| 13,453 | 8/1855 | Buffum | 606/122 |
| D. 320,855 | 10/1991 | Smith et al. . | |
| 617,016 | 3/1899 | Heyns . | |
| 667,447 | 2/1901 | Miller . | |
| 674,738 | 5/1901 | Mills . | |
| 897,289 | 1/1908 | Howell . | |
| 1,782,814 | 11/1930 | Froehlich | 606/122 |
| 2,227,673 | 1/1941 | Price . | |
| 2,542,505 | 2/1951 | Gascoigne . | |
| 3,202,152 | 8/1965 | Wood et al. . | |
| 3,592,198 | 7/1971 | Evans . | |
| 3,642,006 | 2/1972 | Wobbe . | |
| 3,765,408 | 10/1973 | Kawai . | |
| 3,988,793 | 11/1976 | Abitol . | |
| 4,014,344 | 3/1977 | Gutiettez . | |
| 4,127,632 | 11/1978 | Anger . | |
| 4,375,948 | 3/1983 | von Holdt . | |
| 4,512,347 | 4/1985 | Uddenberg | 606/123 |
| 4,597,391 | 7/1986 | Janko | 606/122 |
| 4,620,544 | 11/1986 | O'Neil . | |
| 4,633,865 | 1/1987 | Hengstberger et al. . | |
| 4,730,617 | 3/1988 | King . | |
| 4,794,915 | 1/1989 | Larsson . | |
| 4,799,922 | 1/1989 | Beer . | |
| 5,019,086 | 5/1991 | Neward | 606/123 |
| 5,163,944 | 11/1992 | Neward | 606/123 |
| 5,224,947 | 7/1993 | Cooper et al. . | |
| 5,281,229 | 1/1994 | Neward . | |
| 5,308,321 | 5/1994 | Castro . | |
| 5,395,379 | 3/1995 | Deutchman et al. . | |
| 5,507,752 | 4/1996 | Elliott . | |
| 5,569,265 | 10/1996 | Elliott . | |

FOREIGN PATENT DOCUMENTS

| | | |
|---|---|---|
| 0 083 328 | 7/1983 | European Pat. Off. . |
| 0 527 431 A1 | 2/1993 | European Pat. Off. . |
| 1087487 | 2/1955 | France . |

OTHER PUBLICATIONS

O'Grady, Grimovsky, McIlhargie, *Vacuum Extraction in Modern Obstetric Practice*, 1995, pp. 13–21.

Vacca, *Handbook of Vacuum Extraction in Obstetric Practice*, 1992, pp.1–12.

Primary Examiner—Mickey Yu
Assistant Examiner—Justine R. Yu
Attorney, Agent, or Firm—Leydig, Voit & Mayer, Ltd.

[57] ABSTRACT

A vacuum extractor for use in childbirth which enables the baby's head to be easily maneuvered during delivery. The extractor comprises an open cup with an elongated stem having an opening through which a vacuum may be provided within the cup, and a pair of elongated arms coupled to the cup along substantially opposite sides of the cup. The arms are coupled to the cup by living hinges which allow at least one of the arms to be positioned against the rear, closed portion of the cup such that the extractor presents a relatively low profile for facilitating insertion of the extractor during childbirth. Once in position on the baby's head within the womb, the handles provided at the opposite ends of the arms may be used to maneuver the baby's head during delivery.

18 Claims, 2 Drawing Sheets

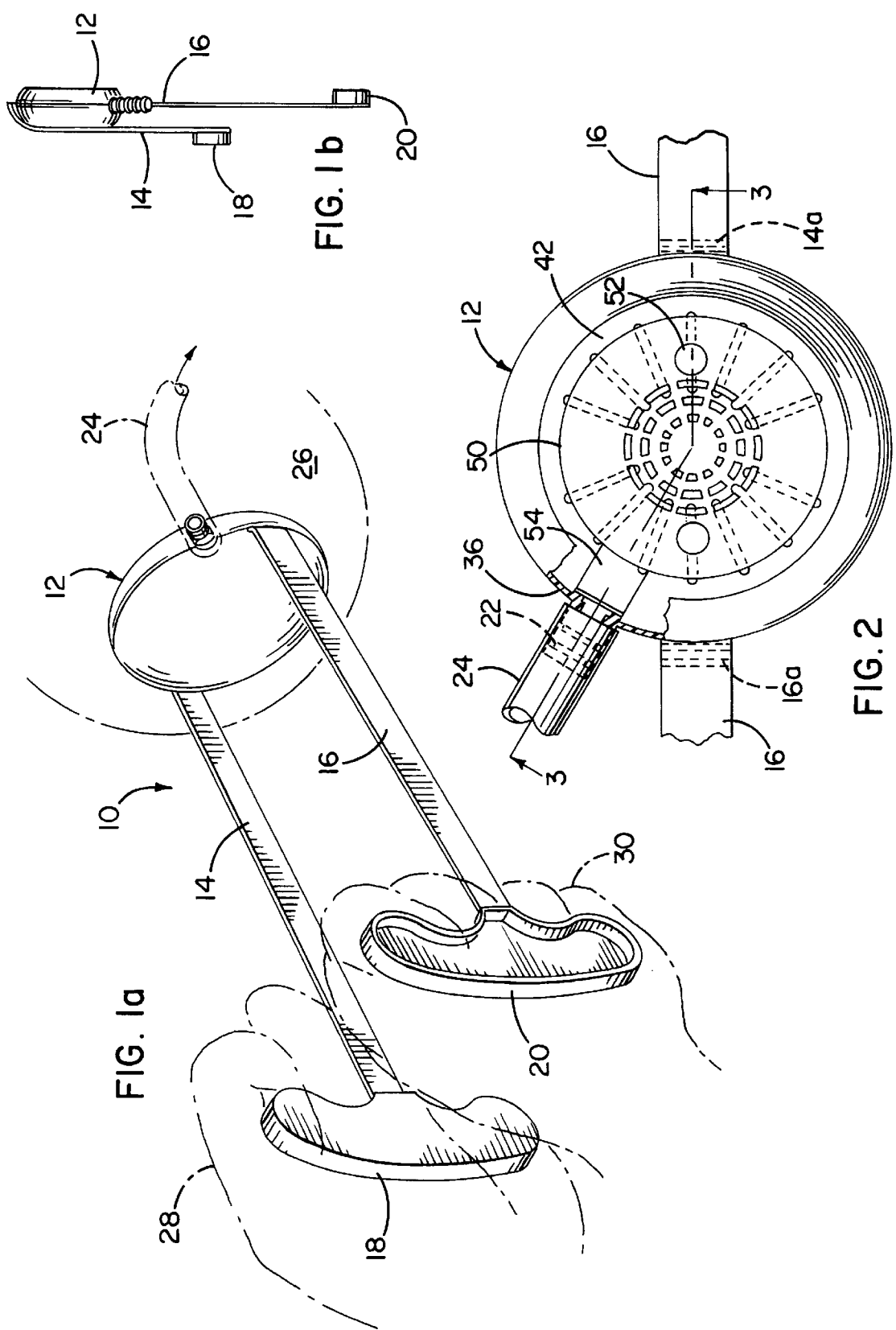

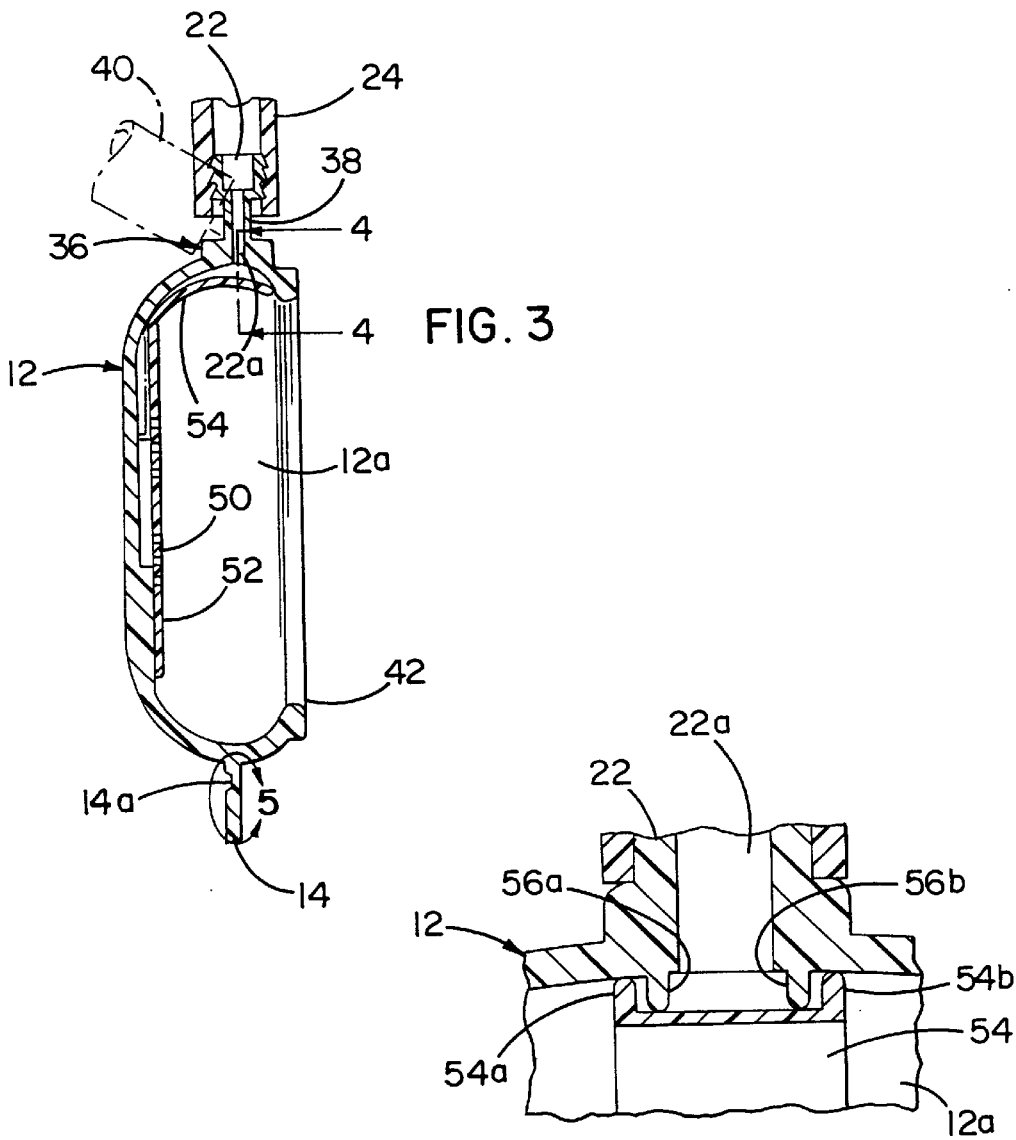
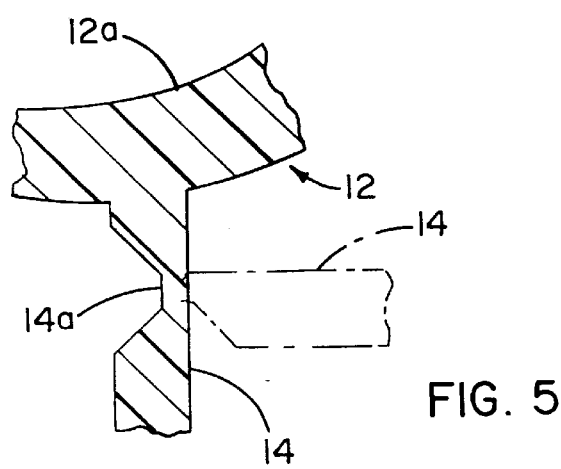

DOUBLE HANDLED VACUUM EXTRACTOR

The present invention relates to apparatus for facilitating the extraction of a baby during childbirth.

BACKGROUND

In some instances during childbirth, a completely natural birth is not possible and assistance must be rendered by the attending physician in order for the child to be delivered. Such assistance may be rendered with forceps and other similar devices, but these devices tend to be bulky and difficult to operate and their use introduces some chances of injury or discomfort to the mother and child. An alternative to forceps is a vacuum extractor device which uses a vacuum cup for attachment onto the head of the child. Joined to the cup is an elongated stem which is used to manipulate the cup. The physician may then apply a pulling force, accompanied by the proper positioning, to be transmitted to the child's head by manipulation of the stem of the device.

An existing obstetrical vacuum extractor is disclosed in U.S. Pat. No. 3,202,152. That patent describes a vacuum operated device, more specifically a vacuum cup, for attaching to the head of a child, and an elongated stem joined to the cup which is used to manipulate the cup, thereby enabling a pulling force to be applied to the child's head. Although that patent describes an effective vacuum extractor, the device can be difficult to manipulate into position onto the child's head.

Another existing vacuum extractor is the Malstrom device which has a vacuum cup with a rubber tube attached thereto. A vacuum is applied to the cup through the rubber tube. A chain is attached at one end to the cup and runs through the tube where it may be grasped by the physician in order to extract the cup. The Malstrom device can only apply a pulling force and does not provide the physician with control to manipulate the child's head.

Another form of vacuum extractor for childbirth is disclosed in U.S. Pat. No. 5,019,086 and in No. 5,163,944, both in the name of the present inventor. The '086 patent discloses an extractor for facilitating positioning onto the head of the child by providing additional flexibility to the vacuum stem of the device to allow bending of the stem to permit the cup of the extractor to be folded into a position substantially parallel to the stem thereby facilitating insertion into the birth canal. The stem includes a handle attached thereto in the vacuum extractor of the '086 patent; whereas an integrally molded handle and stem is disclosed in the '944 patent.

SUMMARY OF THE INVENTION

Although the above-described vacuum extractor devices have been very successful and accepted in the medical community, the present invention provides an improved form of vacuum extractor which incorporates a pair of manipulable handles and arms coupled to the vacuum extractor cup and which maintains the "low profile" features of the extractor disclosed in above U.S. Pat. No. 5,019,086, but further enables the baby to be manipulated without pulling the cup or lifting the cup from the baby's head during the extracting procedure. The construction of the present device allows the medical practitioner to pull on one of the pair of handles of the vacuum extractor in a manner to provide a sideways pull on the head of the baby thereby minimizing the chances of the cup lifting off of the baby's head. Furthermore, the provision of a pair of manipulable handles and arms enables the baby's head to be more easily maneuverable during delivery.

Accordingly, it is the principal object of the present invention to provide an improved apparatus for facilitating the extraction of a baby during childbirth.

Another object of the present invention is to provide a new form of vacuum extractor having a pair of manipulable arms coupled with an extraction cup.

BRIEF DESCRIPTION OF THE DRAWINGS

These and other objects and features of the present invention will become better understood through a consideration of the following description, taken in conjunction with the drawings in which:

FIG. 1a is a perspective view of the vacuum extractor according to the present invention;

FIG. 1b is a diagrammatic illustration thereof in a folded position;

FIG. 2 is an elevational view of the inside of the cup of the vacuum extractor and partially in section;

FIG. 3 is a cross-sectional view taken along a line 3—3 of FIG. 2;

FIG. 4 is a partial cross-sectional view taken along a line 4—4 of FIG. 3; and

FIG. 5 is a partial cross-sectional view illustrating a "living hinge" of the handle/cup assembly as shown in FIG. 3.

DETAILED DESCRIPTION

Turning now to the drawings, an exemplary embodiment of a vacuum extractor 10 of the present invention is illustrated comprising a cup 12 and a pair of arms 14, 16 extending from opposite sides of the cup 12 and terminating in respective handles 18–20. The cup includes a hollow stem 22 to which a flexible vacuum line from a suitable vacuum source can be attached so as to draw a vacuum or lower pressure within the cup 12 to secure the same to the head of a baby, which is diagrammatically indicated at 26, during delivery. The handles 18 and 20 are grasped respectively by the doctor's hands as diagrammatically indicated at 28 and 30. Also, both handles can be grasped by one hand and the baby maneuvered.

The arms 14, 16 are hingeably coupled with the sides of the cup 12 so as to allow one arm (e.g., arm 14) to essentially lie flat across the top or closed side 32 of the cup 12 to thereby provide a low profile configuration as seen in FIG. 1b to facilitate insertion of the vacuum extractor 10 into the mother and attachment of the cup to the head 26 of the child.

The arms 14 and 16 preferably are integrally molded with the cup 12 and include respective living hinges 14a and 16a (only hinge 14a being seen in detail in the drawings, note particularly FIGS. 3 and 5). The living hinges allow the arms 14 and 16 to be hinged or folded in a manner similar to that shown in FIG. 1b to facilitate insertion of the vacuum extractor, as well as to facilitate easy manipulation of the cup 12. The cup 12, arms 14, 16 handles 18, 20 and stem 22 preferably are all molded as a single unit, and preferably of polyethylene.

Turning now to a more detailed discussion of the construction of the cup 12 has a bowl shape as shown, and is substantially identical to the cup shown and described in U.S. Pat. No. 5,019,086. A typical size is approximately two and one-half inches in diameter and approximately seven-eighths in width (from left to right in FIG. 3). Although the stem in the case of the embodiment of U.S. Pat. No. 5,019,086 extends outwardly from the center of the closed side 32, the stem 22 in this case is provided in the side wall 36. The stem 22 also includes a flattened section 38 or area of reduced thickness to allow the stem 22 to bend essentially parallel to the arms 14, 16 essentially as indicated in phantom at 40 in FIG. 3. The stem 22 includes a passageway 22a to allow a vacuum or low pressure to be provided in the interior 12a (note FIGS. 3 and 4) of the cup 12.

The cup 12 includes a ridge 42 (note FIGS. 2 and 3) on the open end of the cup and which has a smooth and rounded contour to provide a gentle and effective contact with the head 26 of the baby.

The cup 12 includes a disk 50 which is secured in any suitable manner inside the cup as by heat welding the same to ribs 52 or the like. Importantly, the disk 50 includes an integrally formed tab 54 (or a separate tab can be provided) which extends over but spaced from the inner end of opening 22a in the stem 22 to prevent skin of the baby's head 26 from being drawn onto the end of the opening 22a which would clog the same and prevent a low pressure from being provided inside 12a the cup 12. The tab 54 includes a pair of integral ribs 54a and b which, along with a pair of ribs 56a and b integrally formed on the inside 12a of the cup 12 adjacent the opening 22a of the stem 22, space the tab 54 slightly from the entry end of the opening 22a so as to allow the reduced pressure to be provided in the interior 12a of the cup 12, but likewise prevent the baby's skin from being drawn into the opening 22a. The disc 50 also preferably is molded of polyethylene.

It will be apparent from the foregoing description of the vacuum extractor 12 that it can be folded into a low profile configuration as shown in FIG. 1b for easy insertion. The arms 14 and 16 and handles 18 and 20 allow the doctor to pull and manipulate the baby's head 26 and, importantly, allow the cup 12 and head 26 to be pulled to the side as necessary without causing the cup 12 to lift off of the baby's head 26 as has sometimes been the case with other vacuum extractors using a central handle stem extending outwardly from the center of the closed surface 32 of the cup 12. Also, the arms 14 and 16 facilitate spreading the walls of the vagina and enable it to open better for facilitating extraction of the baby.

While an embodiment of the present invention as been shown and described, various modifications may be made without departing from the scope of the present invention, and all such modifications and equivalents are intended to be covered.

What is claimed is:

1. A vacuum extractor for use in childbirth comprising a cup with an open front portion, a closed rear portion, and a substantially annular side area intermediate the front and rear portions, said cup having an interior which opens into the open front portion, a stem with an opening therethrough coupled to the cup and communicating with the interior of the cup for enabling an area of reduced pressure to be provided within the interior of the cup, and a pair of elongated arm members coupled to the side area of the cup, said cup and at least one of said arm members being integrally molded, said arm members being movable relative to the cup for facilitating manipulation of the cup during vacuum extraction of a baby during childbirth.

2. The vacuum extractor as in claim 1 wherein the stem extends from the side area of the cup at a location near one of the arm members, the stem having a substantially flattened area near the side area of the cup to facilitate bending of the stem with respect to the cup, and at least one of the arm members being sufficiently bendable to be arched to a position substantially adjacent the closed rear portion of the cup for facilitating insertion of the cup during childbirth.

3. The vacuum extractor as in claim 2 wherein the pair of elongated arm members are disposed substantially diametrically opposite one another and terminate in respective handles for facilitating manipulation of the cup by a physician.

4. The vacuum extractor as in claim 3 wherein the arm members are coupled to the side area of the cup by respective living hinges.

5. The vacuum extractor as in claim 1 wherein the pair of elongated arm members are disposed substantially diametrically opposite one another and terminate in respective handles for facilitating manipulation of the cup by a physician.

6. The vacuum extractor as in claim 1 further including a tab mounted in the cup subjacent the opening in the stem and spaced therefrom to allow reduced pressure to be provided within the cup and prevent skin from a baby's head from being drawn into the opening.

7. The vacuum extractor as in claim 1 wherein at least one of the arm members is sufficiently bendable to be arched to a position substantially adjacent the closed rear portion of the cup for facilitating insertion of the cup during childbirth.

8. The vacuum extractor as in claim 1 wherein the stem includes an area of reduced thickness near the side area of the cup which facilitates bending of the stem.

9. The vacuum extractor as claimed in claim 1 wherein both arm members are resilient.

10. A vacuum extractor for use in childbirth comprising a cup with an open front portion and a closed rear portion, and a substantially annular side area intermediate the front and rear portions, said cup having an interior which opens into the open front portion, a stem with an opening therethrough coupled to the cup and communicating with the interior of the cup for enabling an area of reduced pressure to be provided within the interior of the cup, and two elongated arm members, at least one said elongated arm member being coupled to the side area of the cup, at least one of said arm members being integrally molded with the cup, said arm members being movable relative to the cup for facilitating manipulation of the cup during vacuum extraction of a baby during childbirth.

11. The vacuum extractor as in claim 10 wherein the stem extends from the side area of the cup at a location near one of the arm members, the stem having a substantially flattened area near the side area of the cup to facilitate bending of the stem with respect to the cup, and the other of the arm members being sufficiently bendable to be arched to a position substantially adjacent the closed rear portion of the cup for facilitating insertion of the cup during childbirth.

12. The vacuum extractor as in claim 10 wherein the pair of elongated arm members are disposed substantially diametrically opposite one another, the arm members terminating in respective handles for facilitating manipulation of the cup by a physician.

13. The vacuum extractor as in claim 12 wherein the arm members are coupled to the side area of the cup by respective living hinges.

14. The vacuum extractor as in claim 12 wherein the cup and the arm members are integrally molded.

15. The vacuum extractor as in claim 10 further including a tab mounted in the cup adjacent the opening in the stem and spaced therefrom to allow the reduced pressure to be provided within the cup and prevent skin from a baby's head from being drawn into the opening.

16. The vacuum extractor as in claim 10 wherein the arm member is coupled to the side area of the cup by a living hinge.

17. The vacuum extractor as in claim 10 wherein the arm member is sufficiently bendable to be arched to a position substantially adjacent the closed rear portion of the cup.

18. The vacuum extractor as claimed in claim 10 wherein both arm members are resilient.

* * * * *